United States Patent
Kimani Mwangi (10) Patent No.: US 8,122,891 B2
(45) Date of Patent: Feb. 28, 2012

(54) SUCTION THERAPY APPARATUS AND METHOD

(75) Inventor: Anthony P. Kimani Mwangi, Atlanta, GA (US)

(73) Assignee: Dreamscape Medical LLC, Atlanta, GA (US)

( * ) Notice: Subject to any disclaimer, the term of this patent is extended or adjusted under 35 U.S.C. 154(b) by 380 days.

(21) Appl. No.: 12/419,413

(22) Filed: Apr. 7, 2009

(65) Prior Publication Data

US 2009/0250071 A1   Oct. 8, 2009

Related U.S. Application Data

(60) Provisional application No. 61/123,306, filed on Apr. 7, 2008.

(51) Int. Cl.
  *A61F 5/56* (2006.01)
  *A61H 7/00* (2006.01)

(52) U.S. Cl. ............................ 128/848; 601/6

(58) Field of Classification Search ............ 128/202.28, 128/200.24, 202.29, 203.11, 204.23, 204.18, 128/DIG. 23; 600/41, 43, 44; 601/39, 41–44, 601/6–11
See application file for complete search history.

(56) References Cited

U.S. PATENT DOCUMENTS

| | | | |
|---|---|---|---|
| 4,366,815 A | 1/1983 | Broomes | |
| 4,715,367 A | 12/1987 | Crossley | |
| 5,222,478 A | 6/1993 | Scarberry et al. | |
| 5,343,878 A | 9/1994 | Scarberry et al. | |
| 5,592,938 A | 1/1997 | Scarberry et al. | |
| 6,123,071 A * | 9/2000 | Berthon-Jones et al. | 128/204.18 |
| 7,743,768 B2 * | 6/2010 | Ho et al. .................. | 128/206.24 |
| 2003/0167018 A1 | 9/2003 | Wyckoff | |
| 2005/0098176 A1 | 5/2005 | Hoffrichter | |
| 2006/0069357 A1 * | 3/2006 | Marasco ........................ | 604/289 |
| 2006/0266369 A1 | 11/2006 | Atkinson et al. | |
| 2007/0221231 A1 | 9/2007 | Macken | |
| 2007/0277818 A1 | 12/2007 | Chen | |
| 2009/0177124 A1 | 7/2009 | Silwa et al. | |

FOREIGN PATENT DOCUMENTS

WO   9634586 A1   11/1996

* cited by examiner

*Primary Examiner* — Patricia Bianco
*Assistant Examiner* — Tarla Patel
(74) *Attorney, Agent, or Firm* — Hunton & Williams LLP

(57) ABSTRACT

A suction device includes a membrane-covered walled enclosure from which pressure can be reduced therein, including through desired fluid removal from the enclosure, below ambient external air pressure to apply suction therapy to treat medical conditions, including sleep breathing disorders.

13 Claims, 6 Drawing Sheets

Fig_5

Fig_6

Fig_7

Fig_8

Fig_9

SUCTION THERAPY APPARATUS AND METHOD

CROSS-REFERENCE TO RELATED APPLICATIONS

This application claims the benefit of priority of U.S. provisional application No. 61/123,306, filed Apr. 7, 2008, which is incorporated herein by reference in its entirety.

BACKGROUND

The present invention relates generally to application of suction for medical treatment. Therapeutic application of suction to the body can be used to treat a wide range of conditions, including, for example, muscular, pulmonary, lymphatic and circulatory conditions. In some embodiments, the invention can specifically be adapted for sleep breathing therapy, and more specifically, to provide apparatuses and methods for treating sleep disordered breathing, such as snoring, upper airway resistance syndrome and obstructive sleep apnea, with suction.

There is an ongoing unprecedented global pandemic of obesity resulting from radical changes in lifestyle. In addition, advances in medicine and public health have reversed the morbidity and mortality of many infectious diseases, resulting in longer human life expectancies. The obesity crisis transcends age, gender, cultural and socio-economic lines, and is resulting in tremendous increases in obesity related illnesses such as high blood pressure, diabetes, heart disease and obstructive sleep apnea (OSA).

OSA is a breathing disorder caused by excess fat deposition around the throat and neck that compresses the upper airway when an obese person lies down. During sleep, this causes snoring and recurrent interruption of breathing due to periodic obstruction of airflow at the level of the trachea (windpipe) during inhalation. Repetitive sleep disruption by abnormal breathing leads to chronic sleep deprivation that manifests as daytime fatigue and sleepiness, driving and work related accidents, and lower overall productivity.

OSA affects millions of people globally, most of whom are not treated due to poor access to diagnostic centers and the prohibitively high price of diagnosis and treatment using the best current technology. Medically significant OSA is thought to affect 24% of adult males and 9% of adult females in the United States. Most of these individuals have mild disease, and it is estimated that 75% or more are undiagnosed. Results from a 2005 poll done by the National Sleep Foundation using the Berlin Questionnaire indicate that as many as one in four American adults are at high risk for OSA. These statistics do not include minors; however, increasingly, OSA is being diagnosed in overweight children.

A minority of these patients have been diagnosed and treated due to a general lack of awareness of this health problem, especially since OSA in children tends to manifests as hyperactivity rather than daytime sleepiness. In addition, African-Americans and Asians are at greater risk for sleep apnea, but all the reasons for this have not been identified. Some non-obese patients also have OSA due to abnormal collapsibility of the trachea.

The health consequences can be serious or even life threatening in those with severe OSA. Low blood and tissue oxygen levels caused by cessation of respiration trigger the release of stress hormones like cortisol and adrenaline. These chemicals cause harmful surges in blood pressure, heart rate and blood sugar. Repetitive cycles of this process may lead to a stroke, heart attack or sudden death.

The current state of the art in treating OSA involves the life-long use of mechanical systems that pump air (sometimes enriched with oxygen) into the trachea via a mask that fits tightly over the nose, mouth or both. This pressurized jet of air called CPAP (Continuous Positive Airway Pressure) counteracts the collapse of the trachea from the weight of fatty tissue deposited over it. This technology is effective, but has the disadvantages of being expensive to purchase and maintain, and uncomfortable and impractical to use. The overall long-term compliance with CPAP is low, and usually only those with the most severe symptoms continue treatment.

OSA can be reversed by major weight loss, but this rarely happens without stomach reduction or bypass surgery that is usually reserved for the most obese patients. Consequently, OSA treatment is usually for life. Less radical surgery involves removing the sagging tissues in the nose and throat, and carving away the back of the tongue to create room for airflow. This procedure has been proven to work in only the mildest forms of OSA. The other approach has been to insert dental prosthetic devices in the mouth during sleep to prevent airway collapse, but again only mild cases respond, and these devices are uncomfortable and may damage the oral cavity.

Recent human clinical research has demonstrated that the critical pressure at which the trachea collapses and limits flow to a maximal level (Pcrit) is a measure of airway collapsibility and depends on the stability of the walls defining the upper airway as well as the surrounding pressure. Pcrit is defined as the pressure inside the upper airway at the onset of flow limitation when the upper airway collapses. Pcrit may be expressed as: Pcrit=Pin−Pout where Pin=pressure inside the upper airway at the moment of airway collapse; and Pout=pressure outside the upper airway (atmospheric pressure).

One approach to treatment of snoring and sleep apnea by using a non-CPAP medical device applying negative pressure in the region of the neck is disclosed by U.S. Pat. Nos. 5,343,878 and 5,592,938. Scarberry et al.'s sheath with a vacuum space does not, however, provide guidance as to device construction for comfortably controlling the application of suction and tissue distension.

An urgent need remains for an effective, controllable and comfortable treatment modality for obstructive sleep apnea.

SUMMARY OF THE INVENTION

In one embodiment, the invention answers these needs with a suction device including a membrane secured on the neck of a subject with a sleep breathing disorder, including snoring, upper airway resistance syndrome or obstructive sleep apnea in order to relieve upper airway obstruction.

The invention includes in various embodiments a walled enclosure with a membrane. In one embodiment the walled surface defines a dome-shaped fluid retaining structure with a membrane covering the aperture to which the structure opens. The suction device is applied with the membrane over the anterior upper airway, either directly or over an insulating material, such as an adhesive drape and the like, so that when the user is sleep breathing, fluid is removed from the device resulting in suction as external air pressure is reduced below the ambient pressure in the windpipe. The greater pressure within the windpipe lifts the soft tissues of the neck against gravity away from the windpipe to provide improved breathing.

In embodiments, a device of the present invention is secured with adjustable straps that wrap comfortably around the neck. In further embodiments, the invention provides an integral chin rest in conjunction with a walled enclosure for comfortable suction and patient support.

In further embodiments, fluid removal and replacement, and thereby corresponding pressure behind the membrane and within the enclosure, is automatically controlled through wired or wireless communication with a breathing monitor, such as adjacent to the nose and/or mouth.

In still further embodiments, the invention is adapted for a variety of medical therapies, including vests, wraps and the like, providing for fluid removal and suctioning of desired tissue areas to treat a range of conditions, including but not limited to, pulmonary, circulatory, lymphatic and muscular conditions.

DETAILED DESCRIPTION OF THE INVENTION

The present invention provides suction therapy devices and methods through fluid extraction to reduce pressure behind a membrane below external air pressure, and applied to bodily tissues. Although embodiments for suction treatment of sleep breathing disorders, including snoring and obstructive sleep apnea, are depicted and described in specific examples, the invention encompasses suction therapy devices and methods for other therapeutic treatment of medical conditions. In non-limiting examples, the present invention is configurable to a variety of shapes, wraps, vests and the like, for treating circulatory, muscular, pulmonary and lymphatic conditions.

For example a suction apparatus of the present invention may be applied to an upper airway, such as worn over the trachea to treat congenital or acquired tracheal stenosis or trachemalacia. In other embodiments, a suction apparatus of the invention, including for example a vest, can be applied to the chest to decrease breathing difficulties such as caused by lung fibrosis, obstructed airways, emphysema, neuromuscular diseases, chest wall restrictions and obesity. In still other embodiments, cardiac output may be increased by reducing intrathoracic pressure in persons with heart failure. Angina pectoris and peripheral venous stasis may also be treated by increasing venous blood return to the heart. In still further embodiments, suction devices of the present invention may be applied to limbs and musculoskeletal tissue areas to improve arterial blood flow in cases such as arterial obstruction or poor wound healing. Lymph flow may also be improved in other embodiments through application of suction therapy to targeted body regions according to the present invention. In still other embodiments, a suction device of the present invention may be adapted with blood collection ports, transport tubing and sterilization means and applied to a bleeding wound of trauma victims to collect blood for subsequent transfusion back to a patient or to others.

Referring now to FIGS. 1 and 3-6, in one embodiment of the present invention a suction device 10 comprises a walled enclosure 20, such as a hollow dome-like portion, hereinafter referred to as "dome" 20. A non-hazardous viscous fluid, such as but not limited to mineral oil, is included within one or more chambers of dome 20. In one embodiment, a biodegradable and non-toxic hydraulic fluid, such as a product based on rapeseed (Canola) vegetable oil may be included in the walled enclosure. Other fluid oils may include those based on ISO 32, ISO 46 and ISO 68 specifications. Further, in other non-limiting embodiments, hydraulic fluids based on one or both of ASTM standards ASTM-D-6006, Guide for Assessing Biodegradability of Hydraulic Fluids and ASTM-D-6046, Standard Classification of Hydraulic Fluids for Environmental Impact, may be used in suction device 10.

In other embodiments, other shapes may be provided as an alternative to dome 20, and such shapes may accommodate one or more fluid chambers therein. In one embodiment, dome 10 may have a diameter of about 6 cm for application to a 70 kg male. However, other dimensions of manufacture for the walled enclosure as adapted to other size individuals, including children, or to a particular treatment or body region to be treated, are understood to be encompassed by the present invention. In some embodiments dome 10 is constructed of durable plastic material and may be provided in variety of colors, including transparent or translucent material. In non-limiting embodiments, silicone, plastic, rubber and like seal material is provided to confine hydraulic fluid in inner chambers of dome 10.

Figure 1:
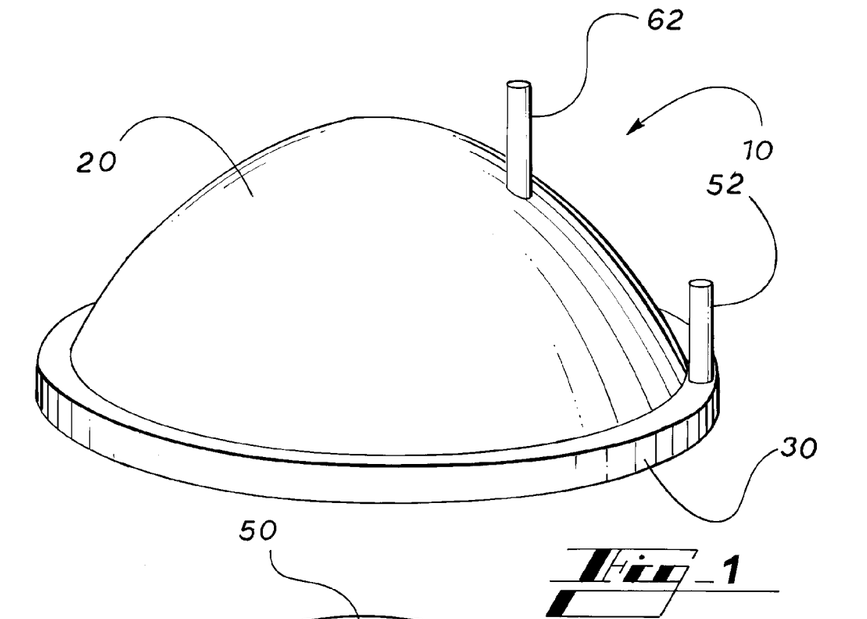
FIG. 1 is a front perspective view from above of a suction device in an embodiment of the present invention.
Figure 2:
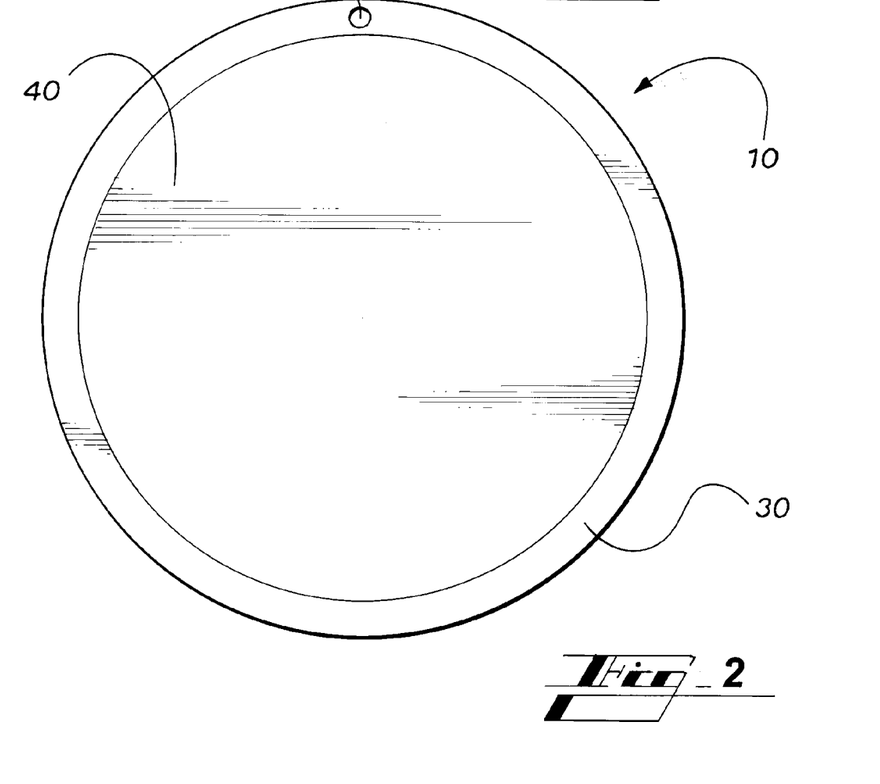
FIG. 2 is a bottom plan view of a suction device in an embodiment of the present invention.
Figure 3:
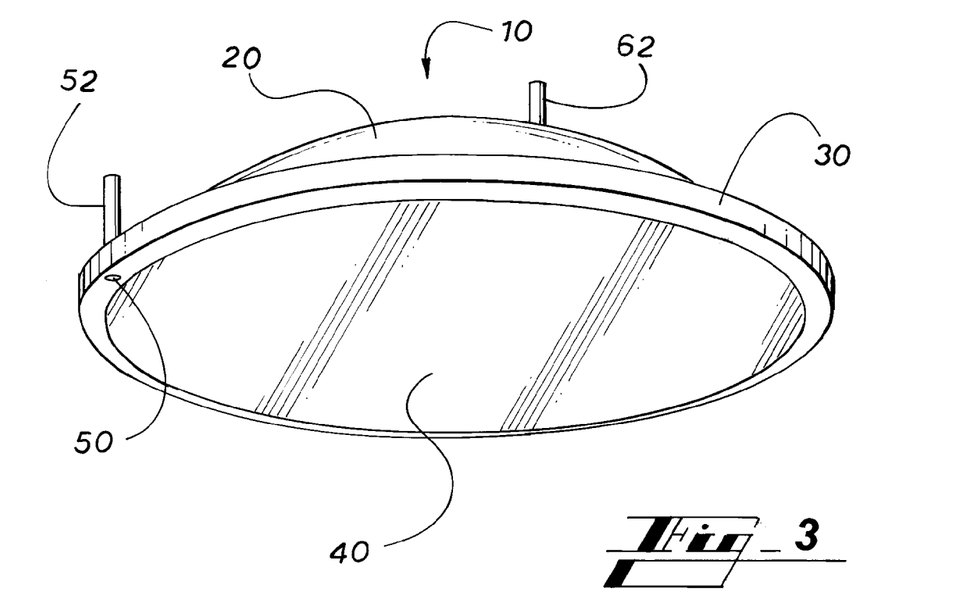
FIG. 3 is a perspective view from below of a suction device in an embodiment of the present invention.
Figure 4:
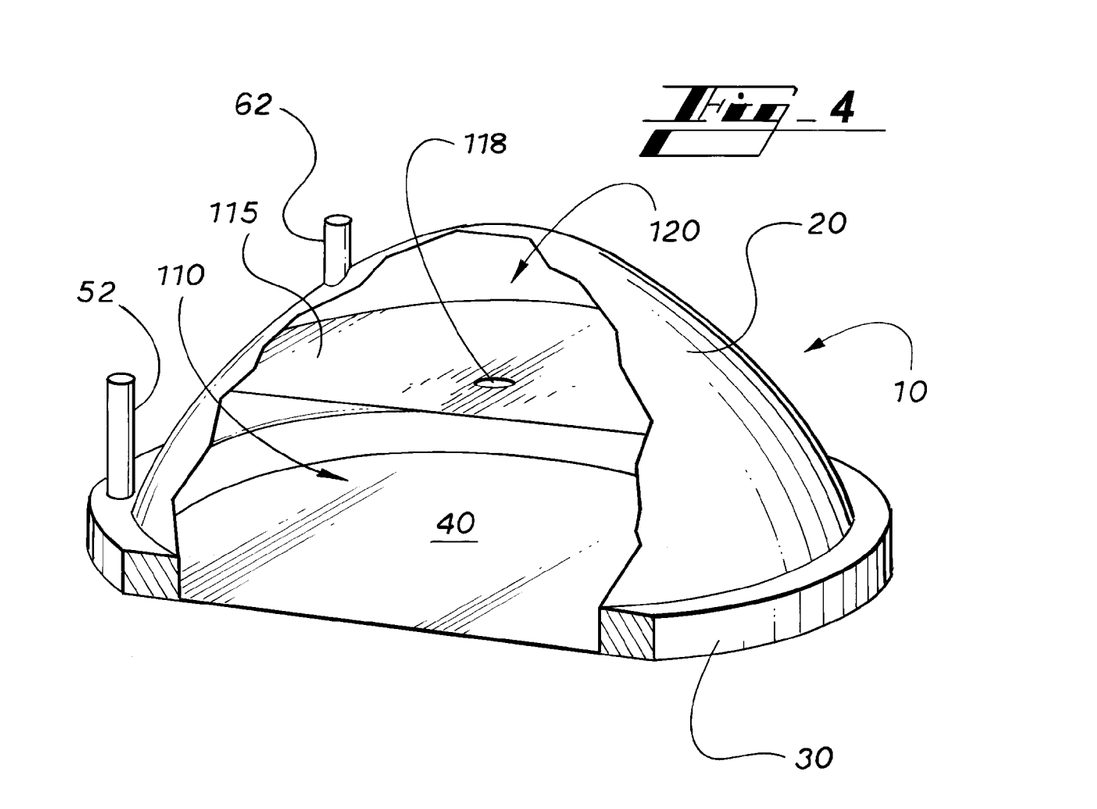
FIG. 4 is a perspective sectional view from above of a suction device in an embodiment of the present invention.
Figure 5:
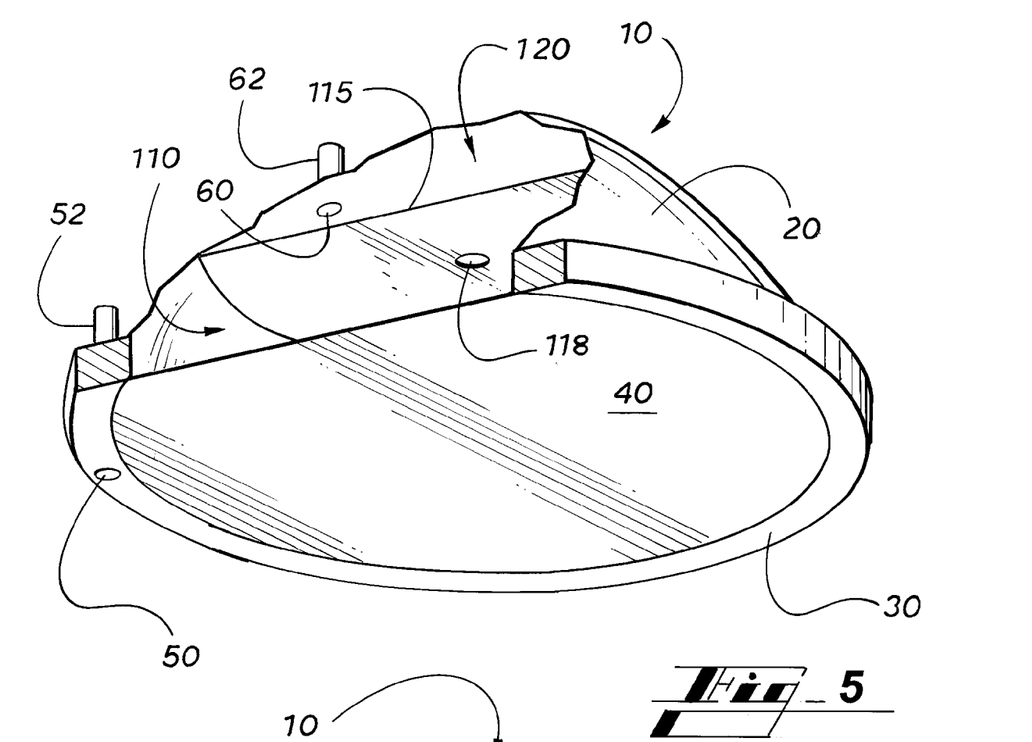
FIG. 5 is a perspective sectional view from below of a suction device in an embodiment of the present invention.

With specific reference to FIGS. 4 and 5, and further reference to FIG. 2, in one embodiment of the invention fluid in primary chamber 110 is retained between an impermeable membrane 40, such as of a pliable plastic, rubber and similar materials, across an aperture of dome 20 and the inner walls of the primary chamber 110. In a depicted embodiment, the primary chamber 110 is connected to a secondary chamber 120 via an orifice 118 in a partition 115 separating the chambers. Partition 115 assists in regulating fluid flow through orifice 118 during extraction or introduction of fluid. In other embodiments of the invention, dome 20 may comprise only a single primary chamber 110, or may comprise multiple chambers with multiple partitions and orifices for fluid retention and removal as desired.

A fluid extraction tube 62 traverses the wall of the secondary chamber 120 and terminates on the exterior surface of the dome 20 to communicate with aperture 60. In some embodiments the fluid extraction tube 62 connects aperture 60 to a power-driven evacuation pump apparatus with a system of electronic controls and sensors. In other embodiments, fluid extraction tube 62 connects aperture 60 to a manual fluid removal/injection device, such as a syringe and the like. The density and volume of the fluid extracted from the primary 110 and secondary chamber 120 of the suction device 10 determines the suction pressure applied.

Suction device 10 provides in various embodiments the equivalent of 5-20 cm water pressure by suction, which is the usual pressure range required to treat OSA with CPAP by overcoming Pcrit. However, in some embodiments the suction device 10 may require less pressure to alleviate a set level of upper airway obstruction than does nasal CPAP because the nasal passages are a source of substantial resistance to airflow. In some embodiments, the excursion of the soft tissues of the neck during suction may be in the 2 mm to 10 mm range depending upon the amount of suction required to overcome Pcrit.

Figure 7:
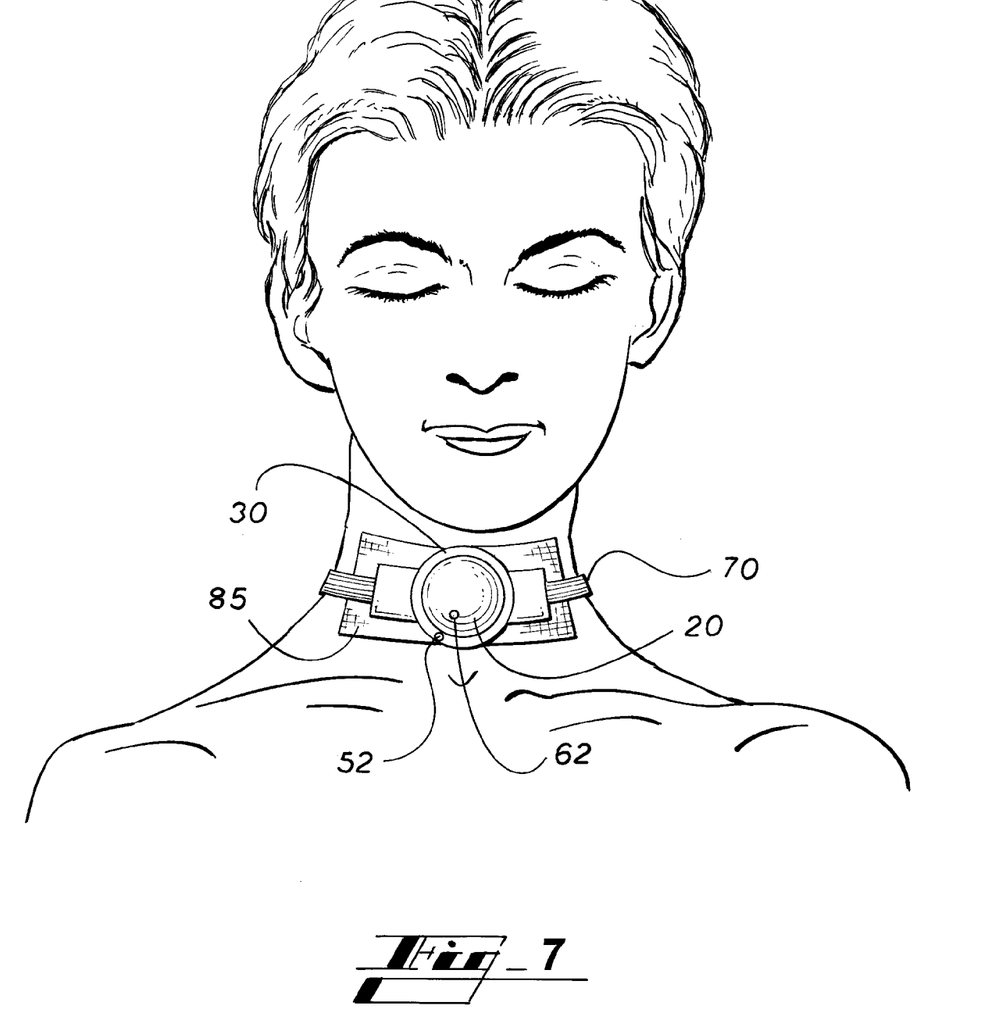
FIG. 7 is a schematic illustration of a suction device applied to a human patient's neck in one embodiment of the present invention.

Referring now to FIG. 7, one embodiment for application of suction device 10 to a patient is shown. Dome 20 is placed centrally over the wearer's throat, with the aperture membrane 40 directly over the skin of the mid-cervical trachea. Dome 20 makes an airtight seal with the skin beneath the aperture membrane 40 by means of a soft adhesive cushion seal 30 made of non-allergenic material, such as but not limited to silicone, attached circumferentially around the perimeter of the aperture of dome 20. In one embodiment membrane 40 may be applied directly to the underlying skin, while in other embodiments an adhesive drape 85 provides a protective layer to prevent the underlying skin from being overstretched during suctioning. In various embodiments, seal 30 may be filled with gels, such as silicone gel, for increased comfort and to optimize air sealing capabilities.

With continuing reference to FIG. 7 and further reference to FIGS. 1-5, the cushion 30 contains an air extraction aperture 50 communicating with air extraction tube 52 through which air trapped in the space between the neck and the cushion 30 and membrane 40 of the dome 20 ("sub-domal air space") may be withdrawn using a manual or automatic air extraction device, such as syringe, pumps and the like, to create and maintain a vacuum seal. In one embodiment, a valve, such as a stop cock and the like, is attached to the air extraction tube 52 and may be closed to maintain the seal. To disconnect the device 10, the valve, such as a stop cock and the like, located on the air extraction tube 52 can be opened to rapidly introduce air into the "sub-domal space", thereby equilibrating the windpipe's internal pressure with atmospheric pressure, and promptly discontinuing suction. The device 10 can thereby be removed from around the neck within a few seconds if necessary. Tubes 52 and 62 in various embodiments are constructed of reinforced plastic, but it will be appreciated that other materials can be used for tubing.

Figure 6:
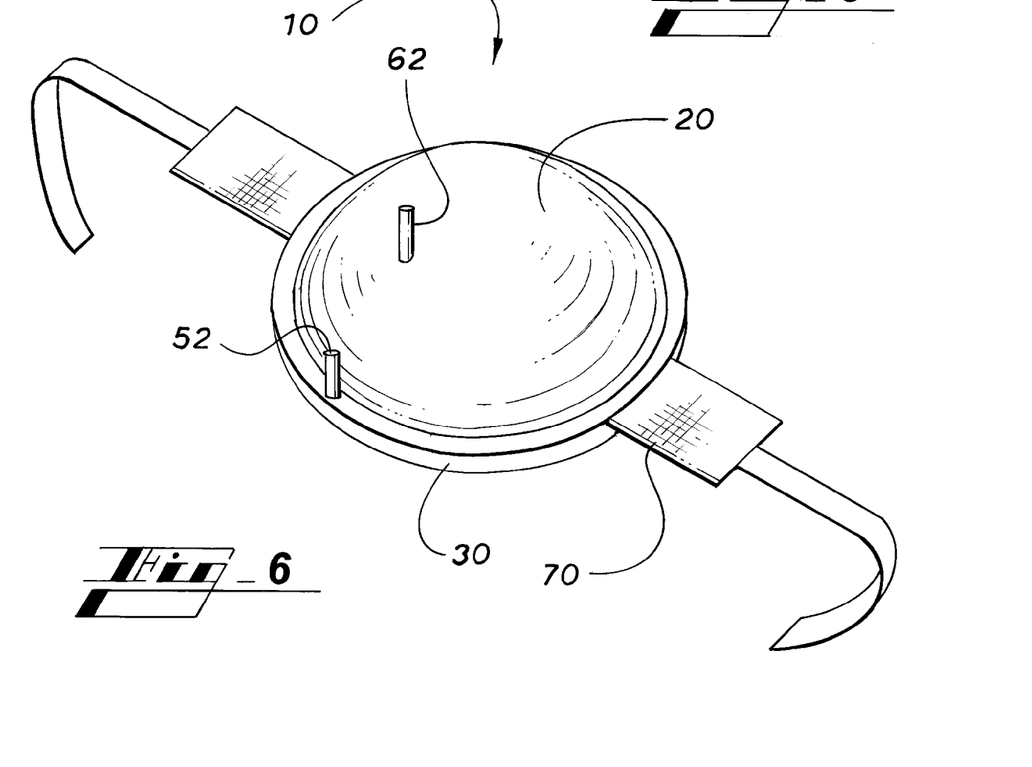
FIG. 6 is a top perspective view of a suction device including straps in an embodiment of the present invention.

With further reference to FIG. 6, in embodiments, the suction device 10 is secured to the subject by means of adjustable straps 70 that go around the neck so that dome 20 and membrane 40 fits snugly over the trachea without an air leak associated with the cushion seal 30.

Referring again to FIGS. 4 and 7, fluid is extracted from the dome 20 while there is an airtight seal around the windpipe. The extraction of fluid 20 from primary chamber 110 creates lower pressure within the dome's inner primary chamber 110 than within a patient's windpipe. The suction device 10 applies suction at membrane 40 to the soft tissues of the neck, gently lifting them against gravity and away from the windpipe when the subject is lying down. With specific reference to FIG. 4, it will be appreciated that in multi-chamber embodiments of suction device 10, fluid in primary channel 110 passes through orifice 118 in partition 115 during fluid extraction.

Figure 8:
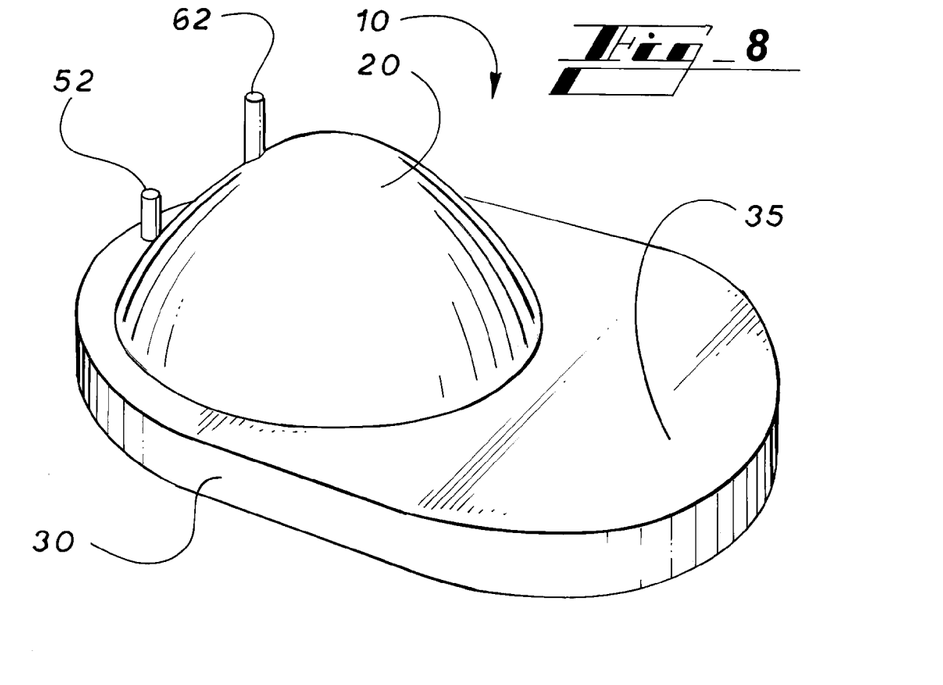
FIG. 8 is a perspective view from above of a suction device including a chin rest in an embodiment of the present invention.
Figure 9:
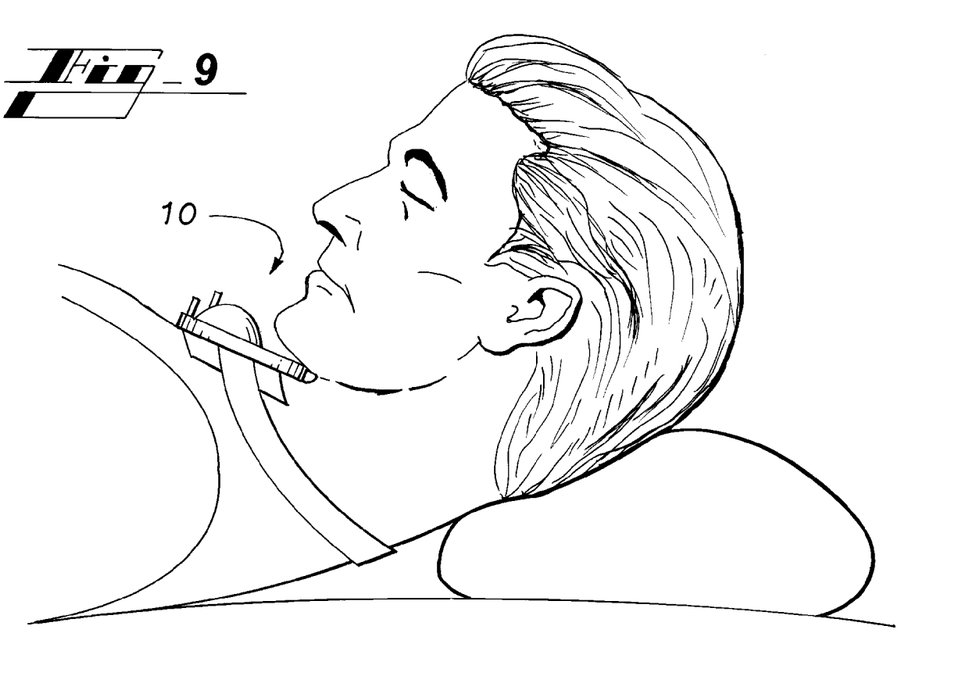
FIG. 9 is a schematic illustration of a suction device including a chin rest applied to a human patient's neck in one embodiment of the present invention.

Referring to FIGS. 8 and 9, in alternative embodiments suction device 10 includes a chin rest portion 35, such as made of a cushion material, including for example same or similar materials to seal 30, to comfortably support the chin of a sleeping patient. A chin rest may include extended portions from seal 30 as shown, as well as in other embodiments one or more cushioned portions coupled over a surface of walled structure 20 that rest adjacent to a patient's chin. Walled structure 20 may also be shaped to extend beneath a person's chin and be covered, or otherwise coupled, with cushion material for comfortably supporting a sleeping patient. Chin rest 35 may be integral to a suction device 10, or may be an ancillary attachment removably coupling to suction device 10, including but not limited to hook and loop attachment and other non-limiting connection means.

In some embodiments, suction device 10 includes a physical or wireless communication connection, e.g. wired, radiofrequency (RF), Bluetooth and the like, to a breathing airflow detection system placed on the subject's nose and/or mouth. In an embodiment, the detection system includes an integrated thermistor and airway pressure transducer. The breathing airflow detection system can distinguish normal respiration from hypopnea (abnormally shallow breathing) and apnea (cessation of breathing for more than ten seconds). The suction force of device 10 may be automatically titrated to airflow. Increased suction force (and consequently soft tissue traction) is applied in response to reduced airflow and vice versa. A self-regulating and dynamic "upper airway obstruction relieving system" results to that function similar to the monitoring and control aspects of an "autoCPAP" device.

In other embodiments of the invention, a single or multi-chambered suction device 10 may utilize air-extraction as an alternative to fluid-extraction in the device 10. In such embodiments, air pressure may be reduced and maintained below pressure level in the windpipe to create suction at membrane 40. Accordingly, extraction tube 62 may communicate with liquid or air pressure regulating devices to control pressure and application of suction of device 10.

Figure 10:
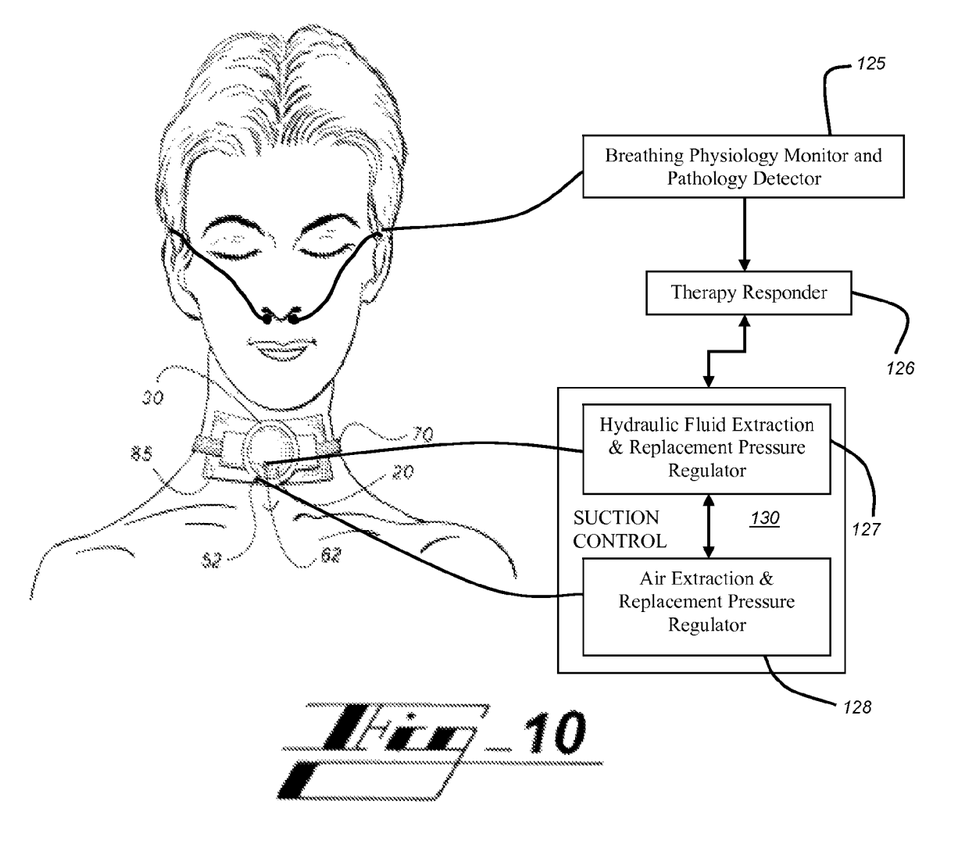
FIG. 10 is a relational block diagram of a suction device and control system in one embodiment of the present invention.

Referring to FIG. 10, in other embodiments of the invention for various medical suction therapies, suction device 10 may include an automatic control system, such as including hardware and software controllers. Suction device 10 and an automatic control system are adapted for the intended application relative to a particular body part. Hardware and software control components may be distributed or centralized into a single control device. In some embodiments, a centralized controller of one or more microprocessors and software control components may be integrated in or on the suction device 10, including walled enclosure 20.

In one embodiment, four control components are provided for automated embodiments of controlling application of suction from device 10, including a Physiology Monitor, a Pathology Detector, a Therapy Responder 126 and a Suction Control 130, collectively referred to as "Control System". It will be appreciated that the functionality of the various components may in alternative embodiments be provided in software and hardware embodiments combining one or more functions.

In one embodiment to relieve sleep disordered breathing, dome 10 and tubes 52 and 62 are coupled to the Control System. The Physiology Monitor assesses the status of cardiovascular, respiratory and other key parameters on a continuous basis. The Pathology Detector processes biological information received from the Physiology Monitor. The Therapy Responder 126 integrates data from the Pathology Detector with preset treatment response algorithms and relays instructions to the Suction Control 130 to implement the treatment protocol by appropriately monitoring and modulating subdomal space pressure. In embodiments, the Control Center sends electronic information about the subject to a remote monitoring station such as a hospital, doctor's office and the like.

In an embodiment of the invention utilizing a Control System to treat sleep disordered breathing with suction device 10, the control components are further described as follows:

1. The Physiology Monitor in one embodiment comprises hardware and software components measuring cardio-respiratory parameters such as the depth, frequency and effectiveness of breathing, oxygen and carbon dioxide levels, pulse rate and blood pressure. The instrumentation of Breathing Physiology Monitor and Pathology Detector 125 is able to detect breaths of normal depth and frequency, abnormally shallow or irregular breaths, and abnormal cessation of breathing effort. Nasal pressure transducers and thermistors may be used in embodiments to monitor and report respiratory status. Instruments that non-invasively measure carbon dioxide level (such as an end-tidal carbon dioxide monitor), and arterial oxygen, pulse and blood pressure (such as a pulse oximeter with pulse transit time capability) may be integrated in embodiments.

2. The Pathology Detector in one embodiment includes a programmed microprocessor discriminating between normal and abnormal respiratory, blood pressure and heart rate patterns. Data from the Physiology Monitor is collated in Pathology Detector, and abnormal results passed on to Therapy Responder.

3. The Therapy Responder 126 in one embodiment includes a programmed microprocessor responding according to customizable algorithms created based on the nature and severity of the abnormal cardio-respiratory data received from the Pathology Detector. Therapy Responder 126 provides orders to modify suction pressure as electronically communicated to the Suction Control 130.

4. The Suction Control 130 monitors and sets subdomal pressure. The suction force of the apparatus is determined by the volume of hydraulic fluid removed from the inner chamber or chambers of dome 20. This volume is controlled in embodiments by a miniature electric pump of hydraulic fluid extraction and replacement pressure regulator 127 that either forces fluid out of the dome 20 via the fluid extraction tube 62 to increase suction, or pumps (or passively allows) the fluid back into the dome 20 to reduce suction. The subdomal pressure is monitored by a connection to the air extraction tube 52 that is connected to air extraction and replacement pressure regulator 128. This embodiment of the invention allows accurate and precise control of the pressure in the subdomal air space.

In embodiments, prior to falling asleep, the subject with sleep disordered breathing correctly positions the suction apparatus 10 in the neck region and the subject interface components of the Physiology Monitor are attached. The Control Center is properly connected to the correct ports on the dome 20. When initially applied to the neck before sleep, the traction force on the soft tissues is minimal. When the subject falls asleep and the first abnormal cardio-respiratory data are collected by the Physiology Monitor, the data are analyzed by the Pathology Detector, and forwarded to the Therapy Responder. When the Therapy Responder determines the response it transmits a command to the Suction Control, turning the fluid pump on, and thereby incrementally reducing subdomal pressure below atmospheric pressure. This process continues until the Physiology Monitor reports complete resolution of upper airway obstruction.

The pump is turned on and off during sleep as needed to maintain the lowest tracheal dilating force necessary to overcome upper airway obstruction. The sensitive and rapid response of the feedback loop between the Physiology Monitor and the Suction Control allows the subject to sleep comfortably since wide swings in subdomal pressure causing uncomfortably large changes in tracheal diameter are avoided.

The Control Center in embodiments is electrically powered with a rechargeable battery, power cord and the like. The Control Center can be attached to sensors on the subject's body, and to the suction apparatus using cables, or in other embodiments can communicate using wireless technology, including RF, Bluetooth and the like.

In embodiments, Suction Control physically couples to the suction device 10 via the air extraction tube 52 and the fluid extraction tube 62. Alternatively, the Control Center can be integrated into the suction device 10 as a single unit.

In other embodiments of the invention, a suction device 10 may be used as a complement and concurrently with a CPAP device, including with an independent or a common automatic control center for coordinated patient monitoring and operation of each device. In such embodiments, suction device 10 may reduce the necessary pressurized air delivered from the CPAP to provide more comfortable CPAP therapy to a patient. In other embodiments, a suction device 10 may enhance or improve the effects of CPAP use. In further embodiments, a suction device 10 may be used as a complement and concurrently with breathing strips, oral appliances, such as dental prosthetics and jaw adjustment devices, and/or a like combination of a therapy device(s) with suction device 10 to improve results over conventional use of such devices.

Those skilled in the art will recognize that the present invention may be manifested in a variety of forms other than the specific embodiments described and contemplated herein. While the invention has been described with reference to the structures and methods disclosed, it is not confined to the details set forth, but is intended to cover such modifications or changes as may fall within the scope of the following claims.

What is claimed is:

1. An apparatus comprising:
   a walled enclosure including one or more hollow chambers;
   a membrane across an aperture defined by a perimeter of the walled enclosure;
   an aperture in the walled enclosure communicating with at least one of the one or more hollow chambers and coupled to an enclosure pressure regulation device;
   a seal coupled to the perimeter of the walled enclosure and surrounding the membrane; and
   an aperture in the seal coupled to a seal pressure regulation device.

2. The apparatus of claim 1, further comprising a partition defining at least two chambers within at least one of the one or more chambers of the walled enclosure and at least one orifice in the partition.

3. The apparatus of claim 2 further comprising a hydraulic fluid within at least one of the chambers of the walled enclosure.

4. The apparatus of claim 3 wherein the enclosure pressure regulation device is a self-regulating pressure regulation device with a communication connection to a breathing airflow detection system configured for placement directly upon at least one of a nose and mouth.

5. The apparatus of claim 2 further comprising a viscous fluid within at least one of the two chambers.

6. The apparatus of claim 1 further comprising a hydraulic fluid within at least one of the one or more chambers of the walled enclosure and the enclosure pressure regulation device is a hydraulic fluid extraction and replacement device.

7. The apparatus of claim 6 wherein the seal pressure regulation device is an air extraction and replacement device.

8. The apparatus of claim 7 wherein the enclosure pressure regulation device is self-regulating and includes a communication connection to a breathing airflow detection system configured for placement directly upon at least one of a nose and mouth.

9. The apparatus of claim 1 wherein the enclosure pressure regulation device is also the seal pressure regulation device.

10. The apparatus of claim 1 wherein the enclosure pressure regulation device is a self-regulating pressure regulation device with a communication connection to a breathing airflow detection system configured for placement directly upon at least one of a nose and mouth.

11. The apparatus of claim 1 further comprising a viscous fluid within at least one of the one or more chambers of the walled enclosure.

12. The apparatus of claim 1 further comprising a protruding cushion chin rest portion extending outward from the walled enclosure.

13. The apparatus of claim 1 wherein the enclosure is dome-shaped and hemispherical.

* * * * *